(12) United States Patent
Linhardt et al.

(10) Patent No.: US 6,590,110 B1
(45) Date of Patent: Jul. 8, 2003

(54) METHOD FOR SYNTHESIZING C-GLYCOSIDES OF ULOSONIC ACIDS

(75) Inventors: Robert J. Linhardt, Iowa City, IA (US); Tulay Polat, Iowa City, IA (US); Yuguo Du, Beijing (CN)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/806,586

(22) PCT Filed: Mar. 30, 1999

(86) PCT No.: PCT/US99/23214

§ 371 (c)(1),
(2), (4) Date: May 17, 2001

(87) PCT Pub. No.: WO00/18777

PCT Pub. Date: Apr. 6, 2000

Related U.S. Application Data

(60) Provisional application No. 60/102,459, filed on Sep. 30, 1998.

(51) Int. Cl.⁷ ..................... C07D 307/06; C07D 309/06
(52) U.S. Cl. ..................... 549/425; 549/428; 549/453; 549/455
(58) Field of Search ................... 549/425, 426, 549/428, 451, 453, 455; 536/1.11

(56) References Cited

PUBLICATIONS

Pouilly et al., Organic Synthesis, pp. 1391–94 (1991).*
Zjawiony et al., No. 213, Abstract of Papers, 216th ACS Nat. Meeting. 0–8412–3627–5, (Boston, MA) Aug. 1998.*
Mazeas et al., Angew. Chem. Int. Ed. Engl., vol. 34, No. 8 (1995), pp. 909–912.*
Vlaho et al., J. Am. Chem. Soc. vol. 119, No. 6 (1997), pp. 1481.*
Hung et al., Angew. Chem. Int. Ed. Engl. vol. 35, No. 22 (1996), pp. 2671–2674.*
Jarreton et al., Chem. Commun. Jul. 1996, pp. 1661–1662.*
Nagy et al. Tetrahedron Lett, vol. 32(B2) (1991) pp. 3953–3956.*
Luthman et al., J. Org. Chem., vol. 52, No. 17, pp. 3777–3784 (1987).
Tomiyama et al., Society National Meeting, Part 2, Abstract No. MEDI–214 (1998).

* cited by examiner

Primary Examiner—Taofiq Solola
(74) Attorney, Agent, or Firm—Birch, Stewart, Kolasch & Birch, LLP

(57) ABSTRACT

The invention is directed to a method for synthesizing C-glycosides of ulosonic acids, as well as intermediates thereof and C-glycosides prepared by this method.

22 Claims, 12 Drawing Sheets

METHOD FOR SYNTHESIZING C-GLYCOSIDES OF ULOSONIC ACIDS

This application is the national phase under 35 U.S.C. §371 of PCT International Application No. PCT/US99/23214 which has an International filing date of Sep. 30, 1999, which designated the United States of America and was published in English and which claimed priority to U.S. Provisional Application No. 60/102,459, filed Sep. 30, 1998.

TECHNICAL FIELD

The present invention relates to a method for synthesizing C-glycosides of ulosonic acids, as well as intermediates thereof and particular C-glycosides prepared by the method.

BACKGROUND ART

Ulosonic acids are a diverse family of complex monosaccharides that serve important biological functions. The most common ulosonic acids are N-acetylneuraminic acid (NANA), 3-deoxy-D-glycero-D-galactonulosonic acid (KDN) and 3-deoxy-D-manno-2-octulosonic acid (KDO), important constituents of many glycoconjugates, often occupying the non-reducing ends of oligosaccharide chains. Glycoproteins containing NANA, for example, are involved in a number of biological processes including cell interactions with other cells, microorganisms, toxins and antibodies.[1] The biologic functions of ulosonic acids are derived from their size, negative charge and their natural position as the terminal residue on cell surface glycoconjugates. C-glycosides of ulosonic acids are of particular interest for their potential pharmaceutical applications. These are expected to have both improved enzymatic hydrolytic stability and exoanomeric conformation similarity to the corresponding O-glycosides.[2]

The synthesis of C-glycosides is a well established area of carbohydrate chemistry.[3] The utility of glycosyl chlorides in the formation of C-glycosides has been appreciated for some time. Until recently the aglycone portion of this radical pathway was limited to allylsilane, 1,3-dimethoxy benzene.[3a] Sinaÿ[4] and Wong[5] examined the possibility of coupling chloride and ketone (or aldehyde) under $SmI_2$ mediated radical reactions. In the presence of a protecting group at C-2, glycal was produced, in place of the desired C-glycoside. NANA-C-glycoside was reported by Bednarski[6] through NANA-glycosyl chloride with $(nBu)_3SnCH_2CH=CH_2$ and catalytic amount of $[(nBu)_3Sn]_2$, affording 1:1 mixture of NANA-C-glycoside. By using glycosyl aryl sulfones, Beau and co-workers prepared the corresponding 1,2-trans-C-glycosides under Barbier conditions.[7] A similar approach was used in the first examples of the NANA[8] and KDN[9] C-disaccharide synthesis in our laboratory, using pyridyl and phenyl sulfones as nucleophiles. There are two disadvantages of using sulfones as nucleophiles: 1) additional steps are required for their preparation and 2) they often produce a very unpleasant odor.

DISCLOSURE OF THE INVENTION

Accordingly, an object of the present invention is to provide a method for synthesizing C-glycosides of ulosonic acids such as Neu5Ac, by which diastereocontrolled synthesis of α-C-glycosides of ulosonic acids is attained, which is simpler than the known method and free from the unpleasant odor caused by the use of a sulfone derivative.

The present inventors intensively studied to discover that the above-mentioned object may be attained by reacting a halogenated ulosonic acid with an aldehyde or ketone compound in the presence of a lanthanide metal halide, thereby completing the present invention.

That is, the present invention provides a method for synthesizing C-glycosides of ulosonic acids comprising the step of reacting a halogenated ulosonic acid with an aldehyde or ketone compound in the presence of a lanthanide metal halide, such as samarium iodide.

By the present invention, a method for synthesizing C-glycosides of ulosonic acids, by which diastereocontrolled synthesis of α-C-glycosides of ulosonic acids is attained, which is simpler than the known method and free from the unpleasant odor caused by the use of a sulfone derivative, was provided.

BEST MODE FOR CARRYING OUT THE INVENTION

Figure 1:
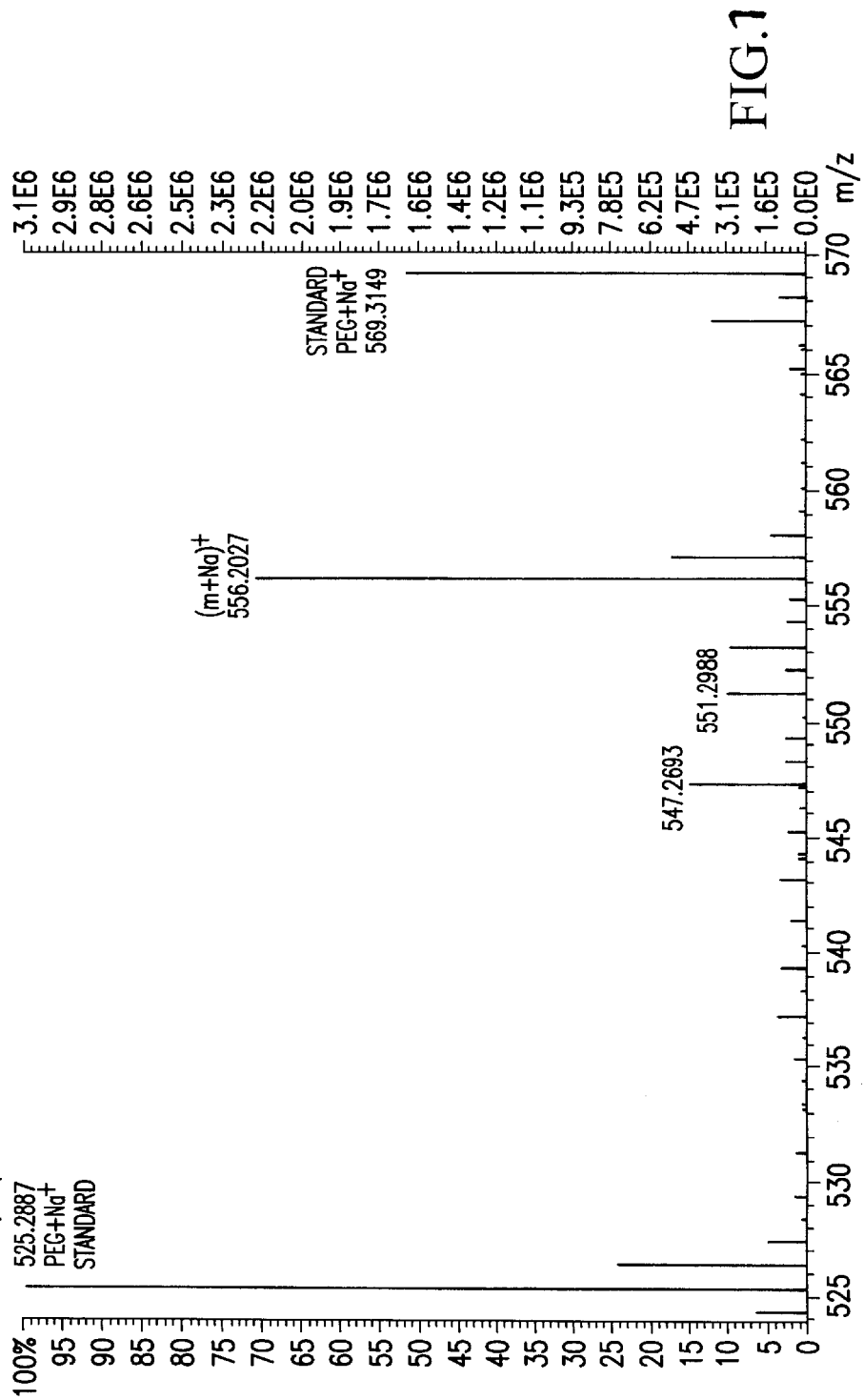
FIG. 1 is positive FAB mass spectra of Compound (3)
Figure 2:
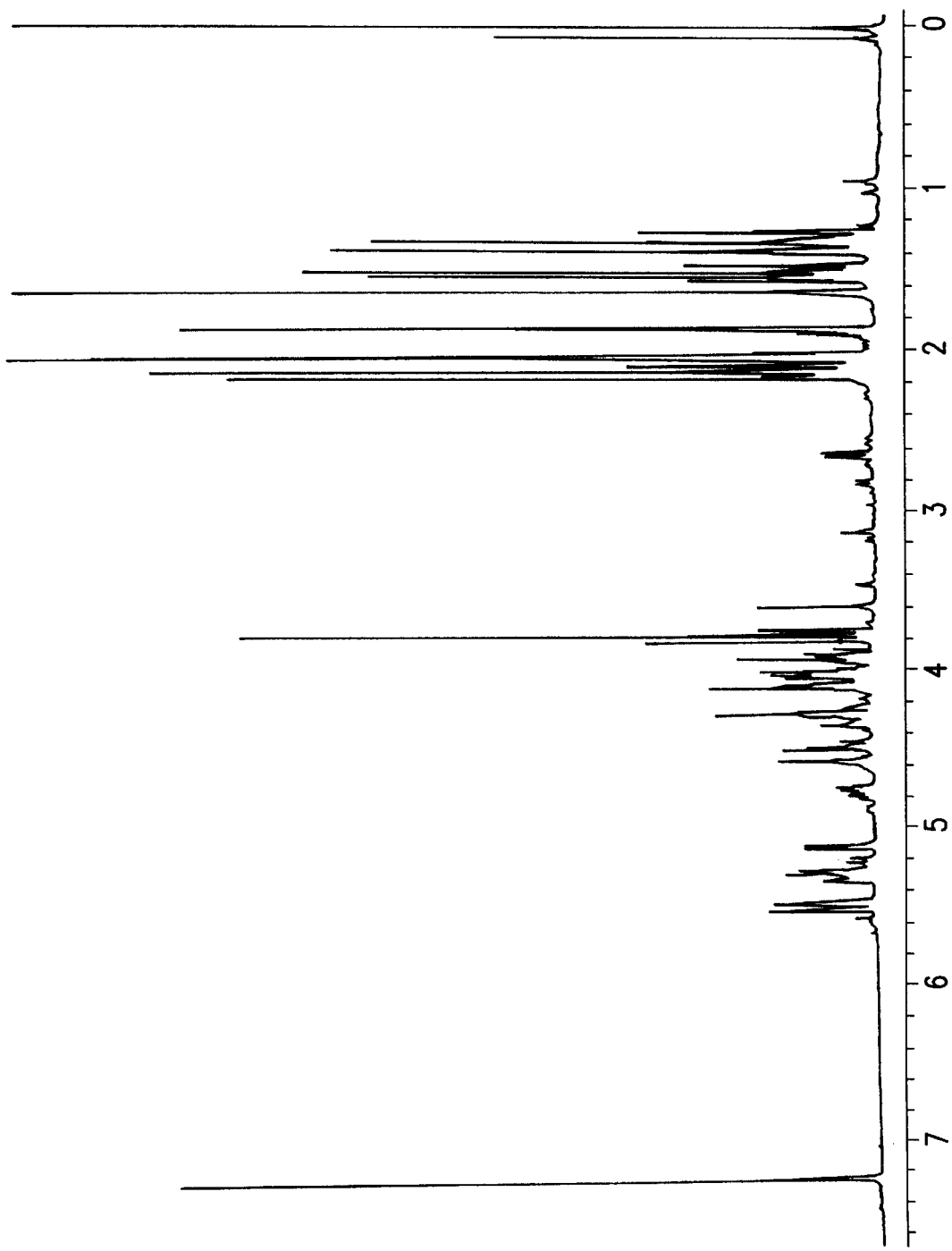
FIG. 2 is $^1$H-NMR spectra of Compound (5) recorded in $CDCl_3$ at 500 MHz.
Figure 3:
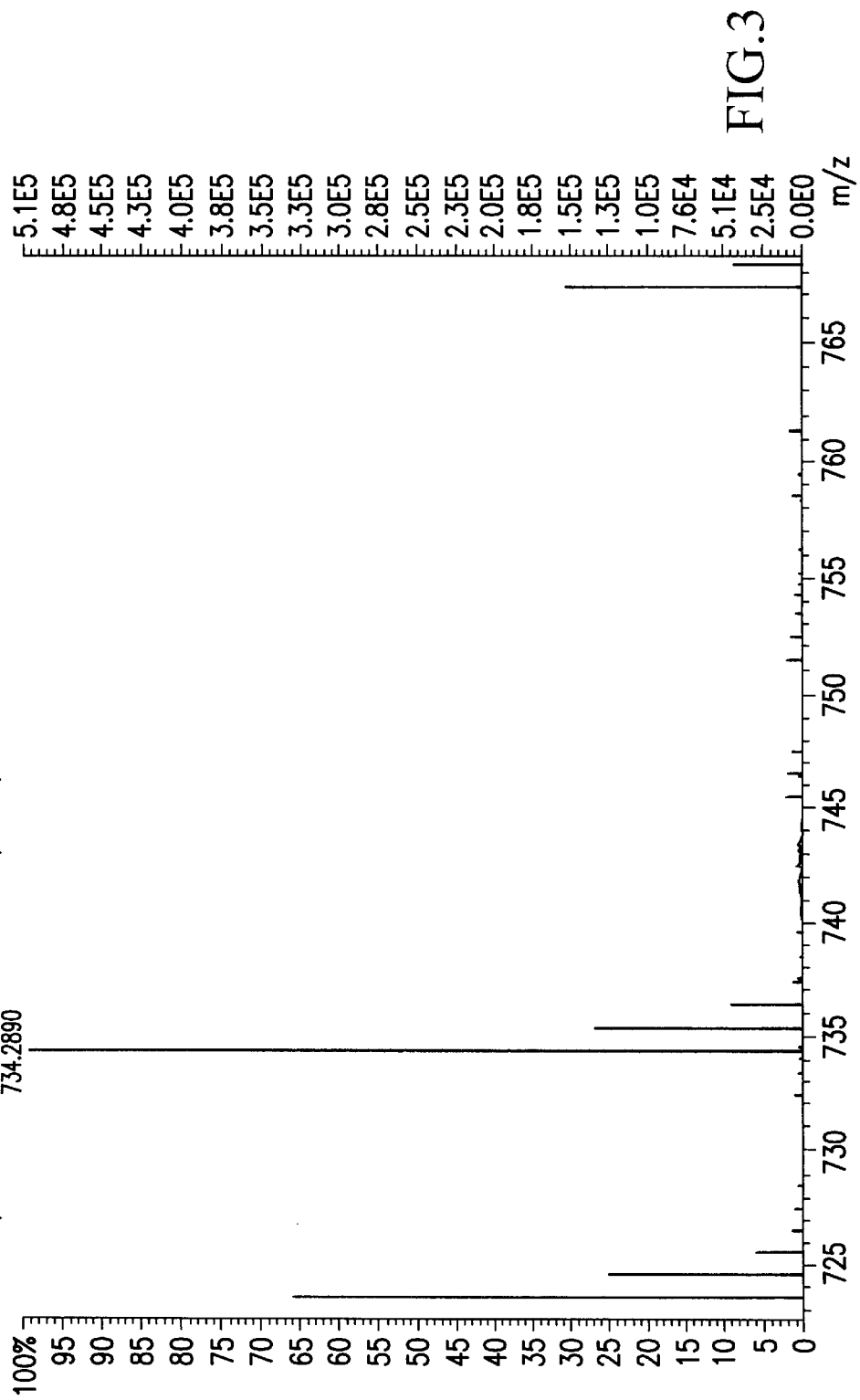
FIG. 3 is positive FAB mass spectra of Compound (5)
Figure 4:
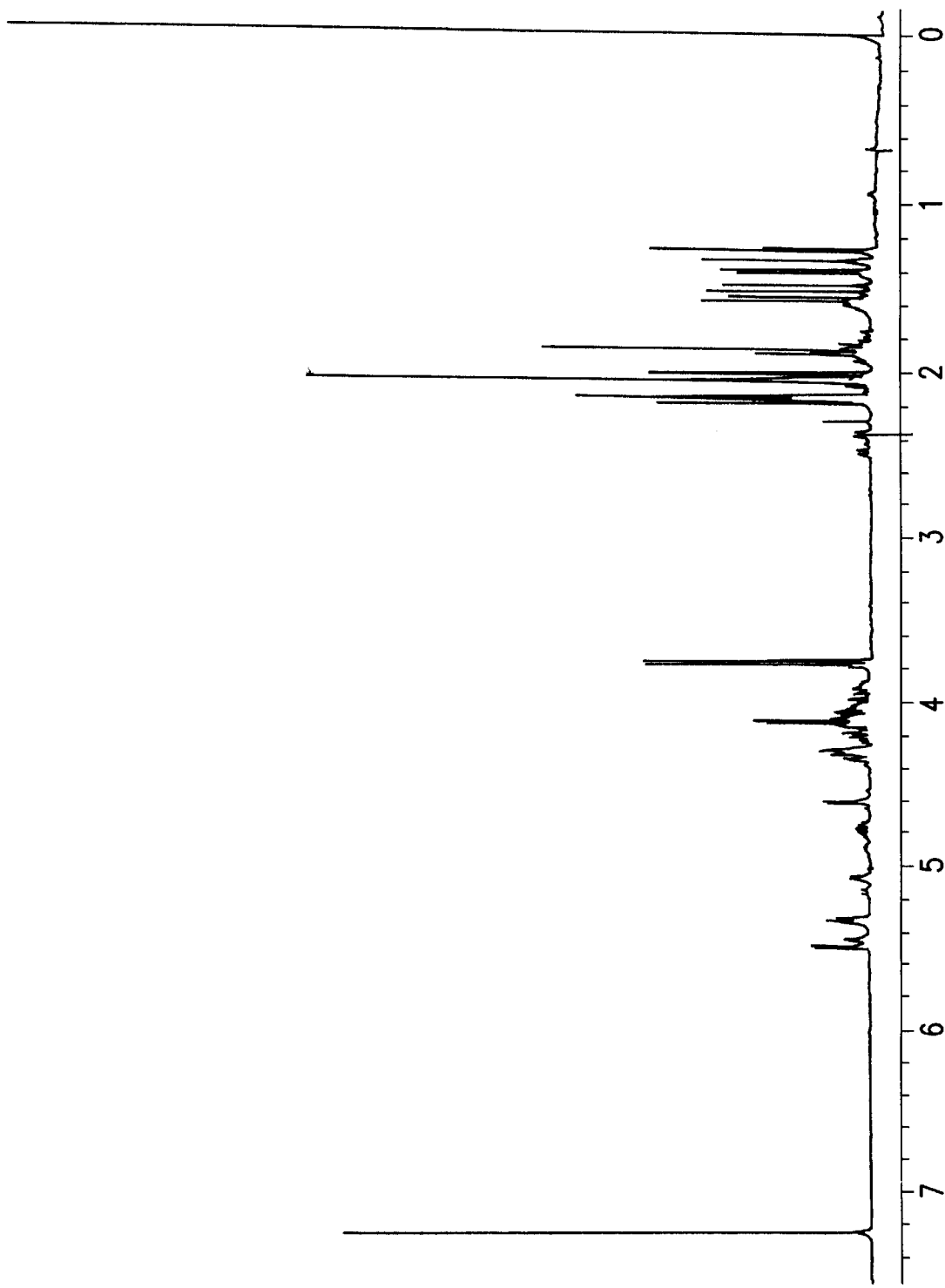
FIG. 4 is $^1$H-NMR spectra of Compound (7) recorded in $CDCl_3$ at 500 MHz.
Figure 5:
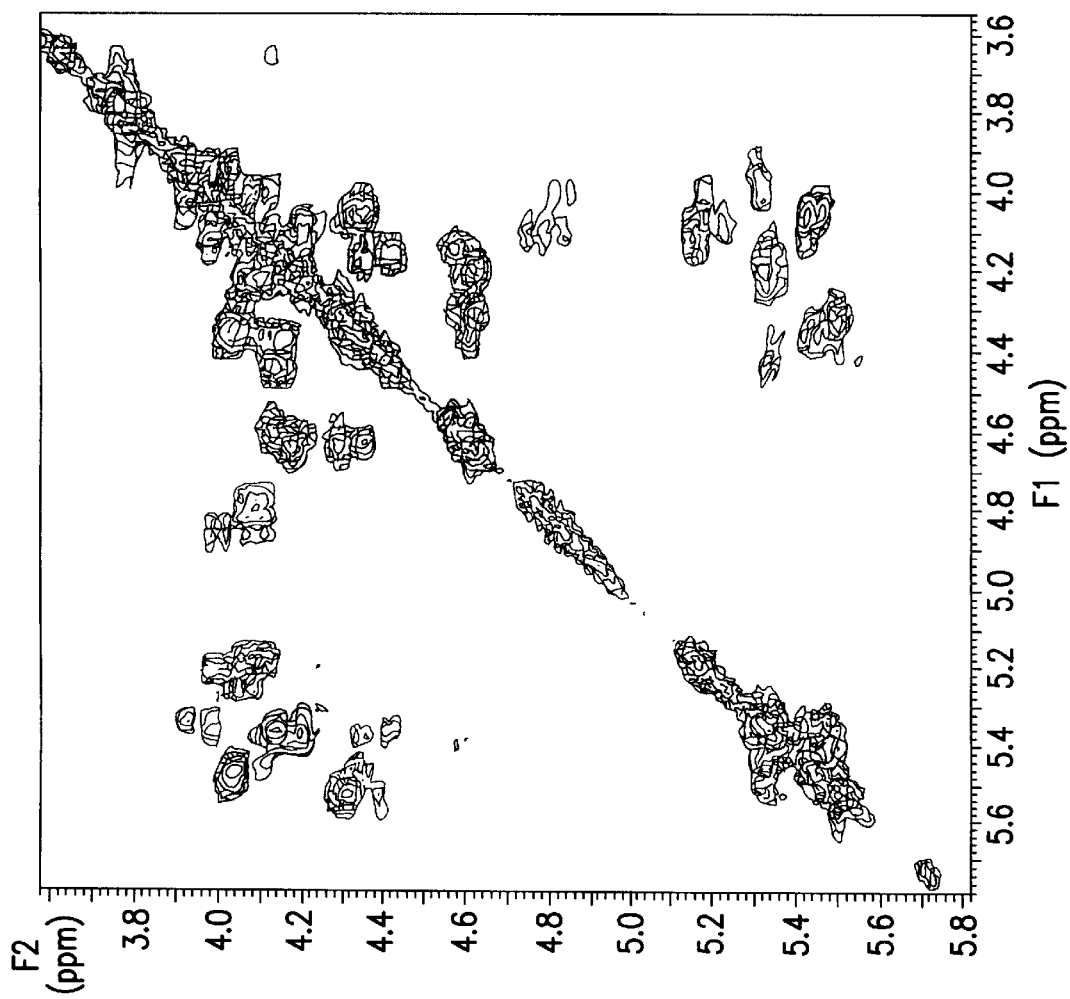
FIG. 5 is two dimensional COSY spectrum of Compound (7)
Figure 6:
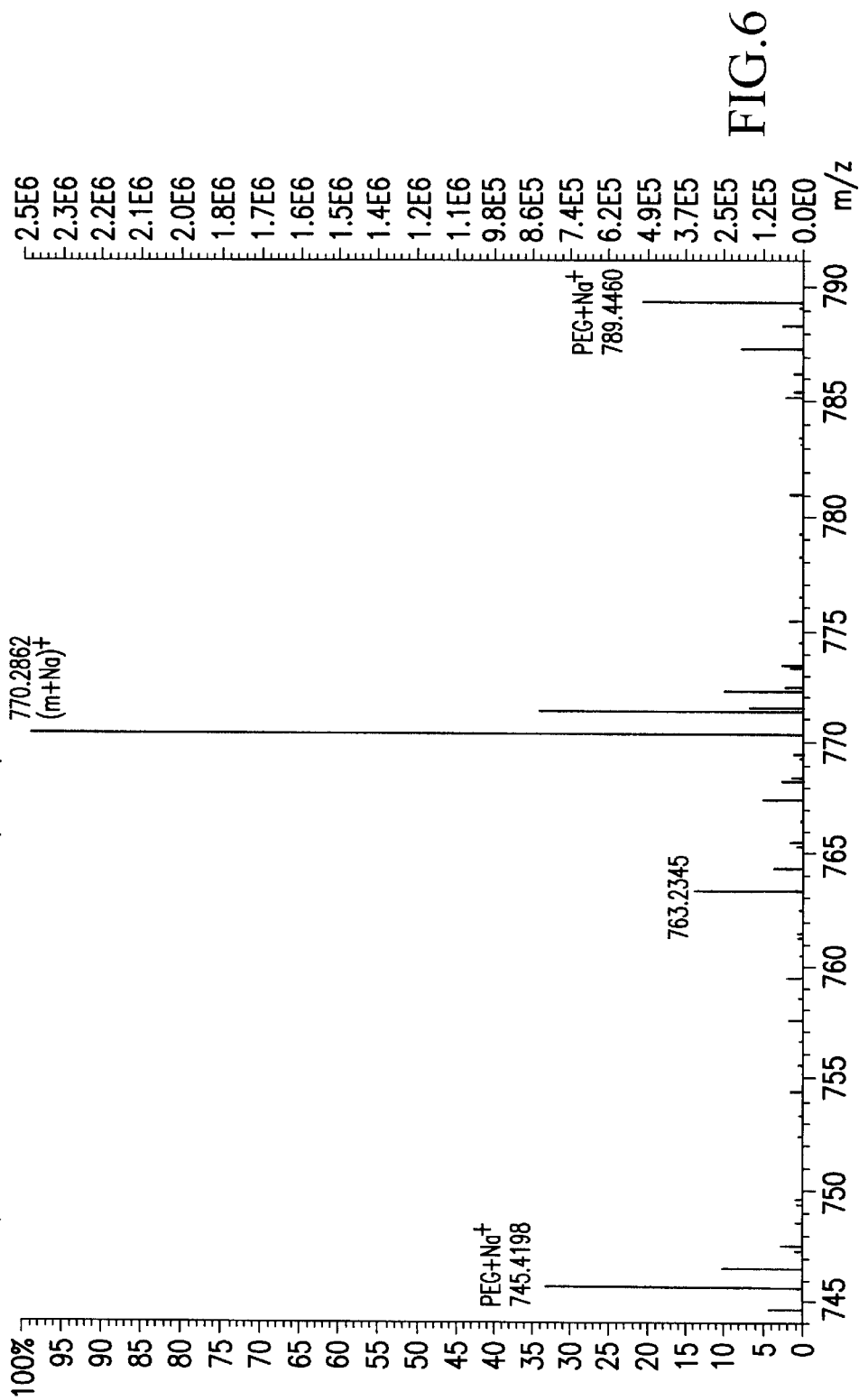
FIG. 6 is positive FAB mass spectra of Compound (7)
Figure 7:
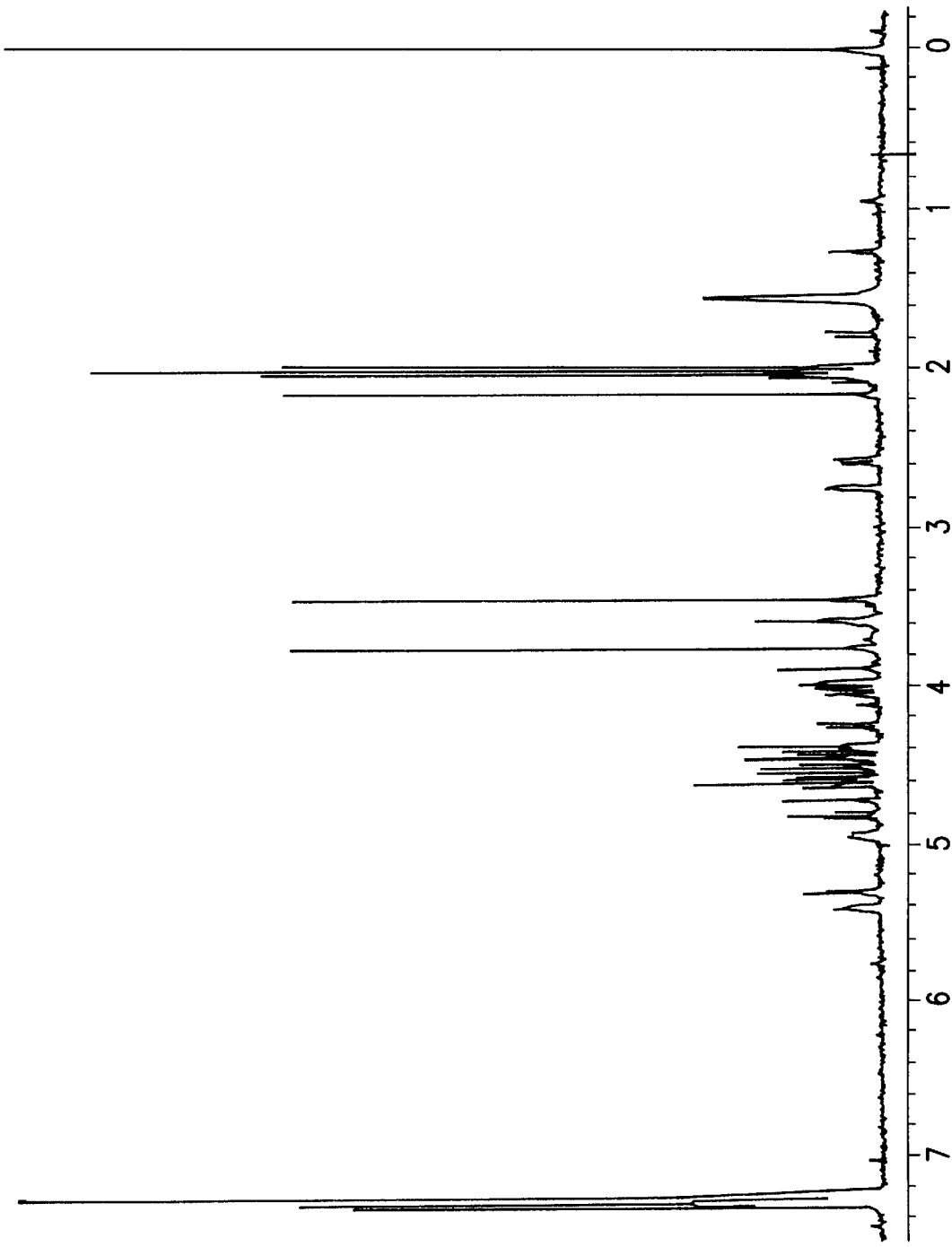
FIG. 7 is $^1$H-NMR spectra of Compound (10) recorded in $CDCl_3$ at 500 MHz.
Figure 8:
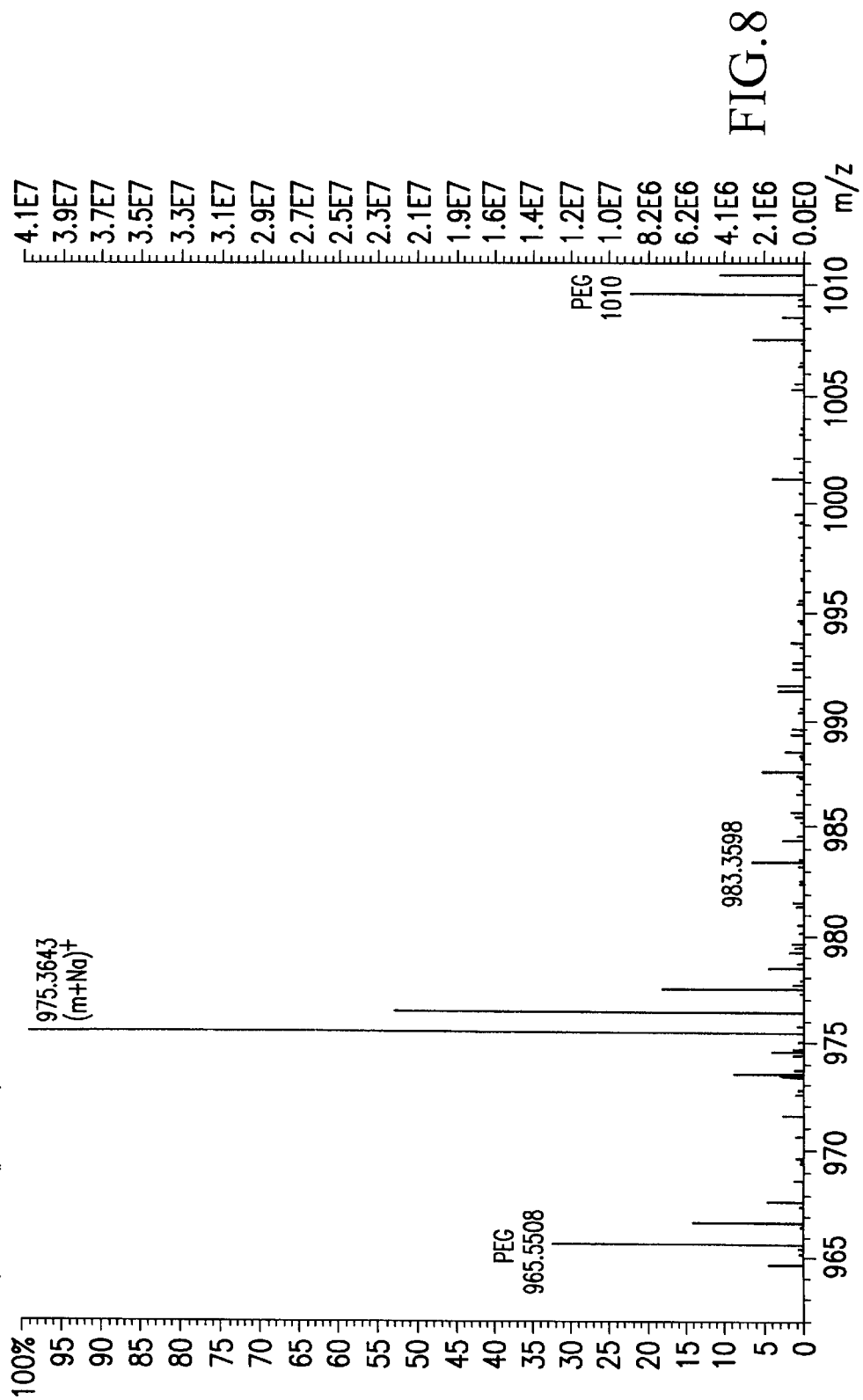
FIG. 8 is positive FAB mass spectra of Compound (10)
Figure 9:
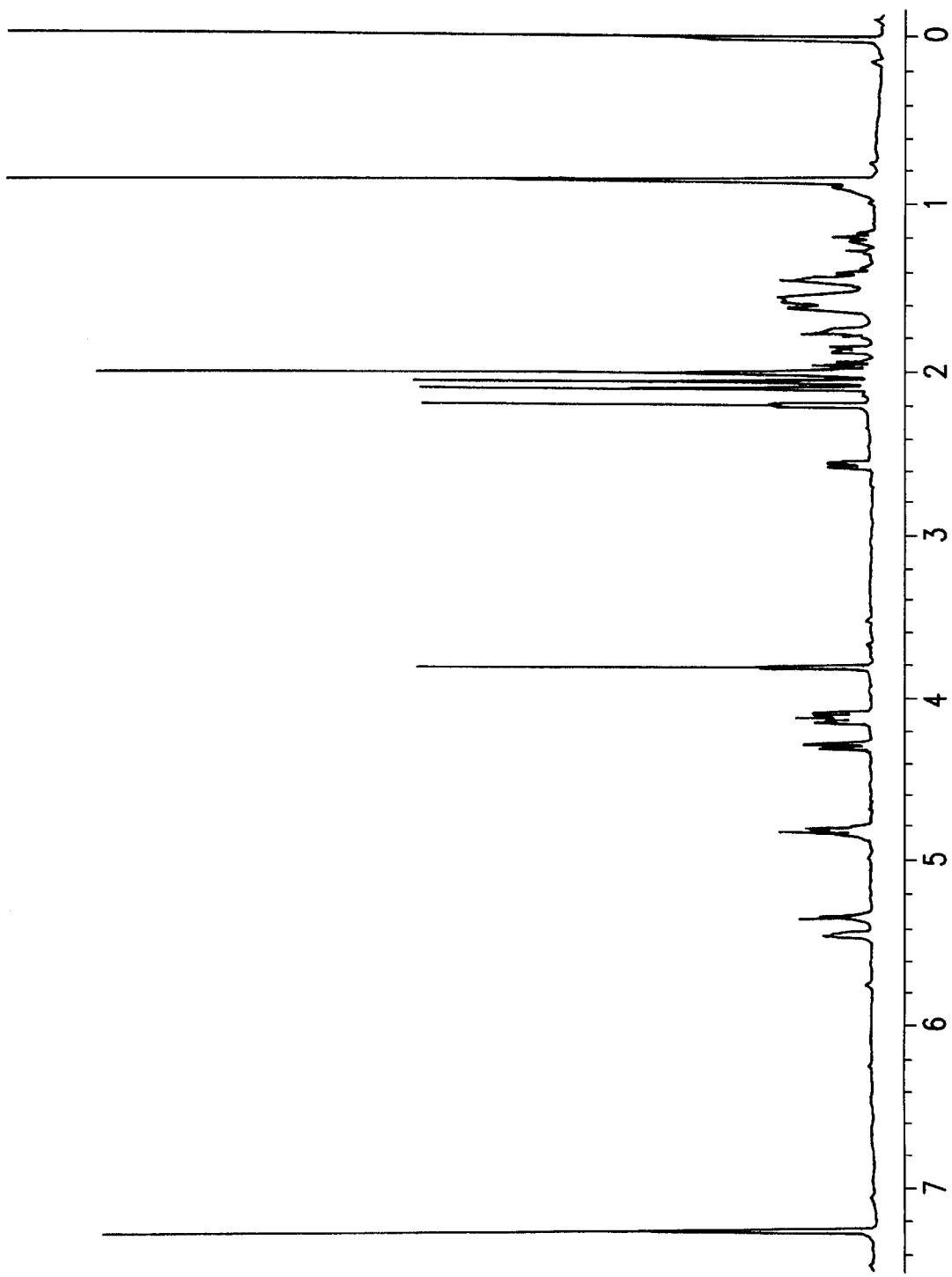
FIG. 9 is $^1$H-NMR Spectra of Compound (12) recorded in $CDCl_3$ at 500 MHz.
Figure 10:
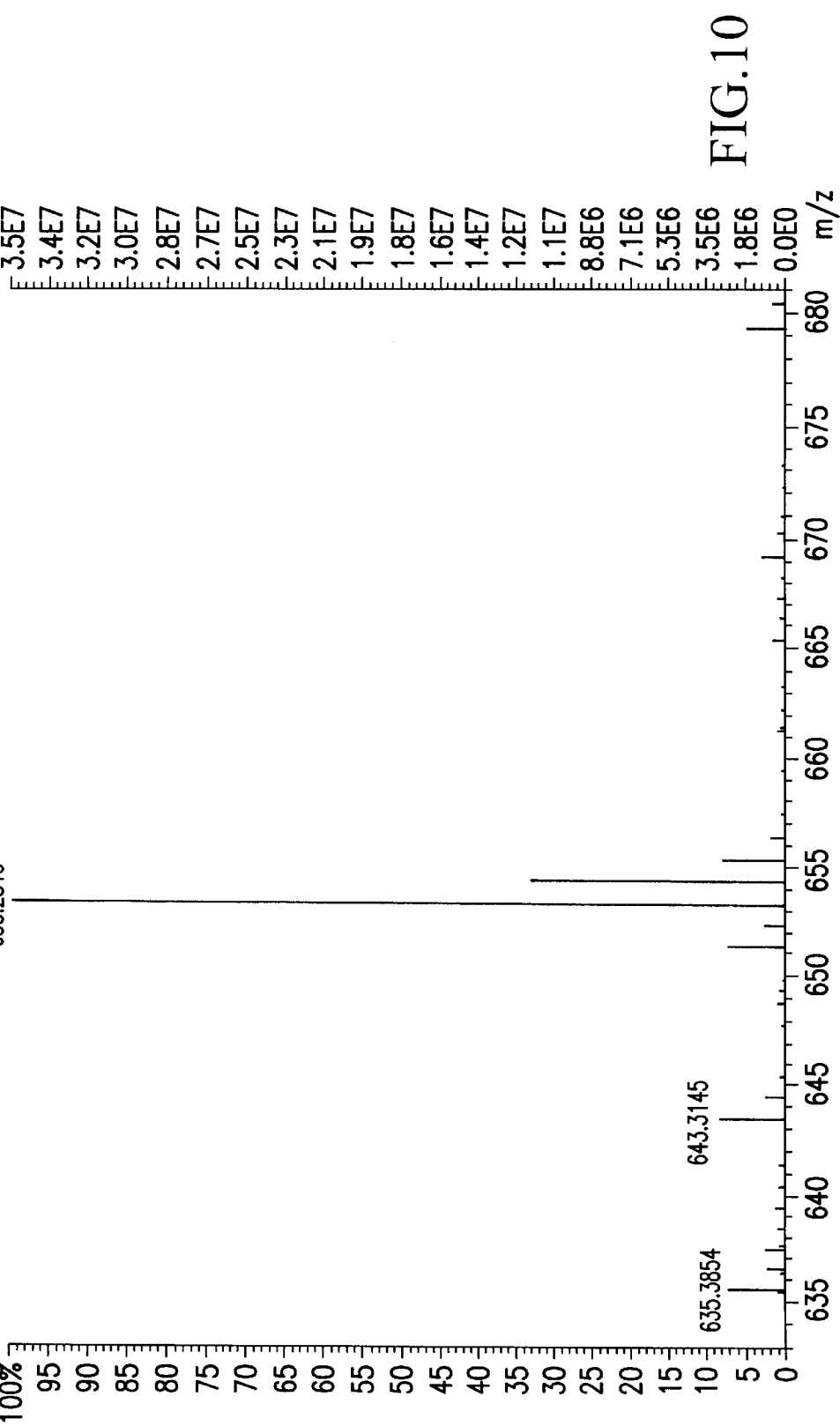
FIG. 10 is positive FAB mass spectra of Compound (12)
Figure 11:
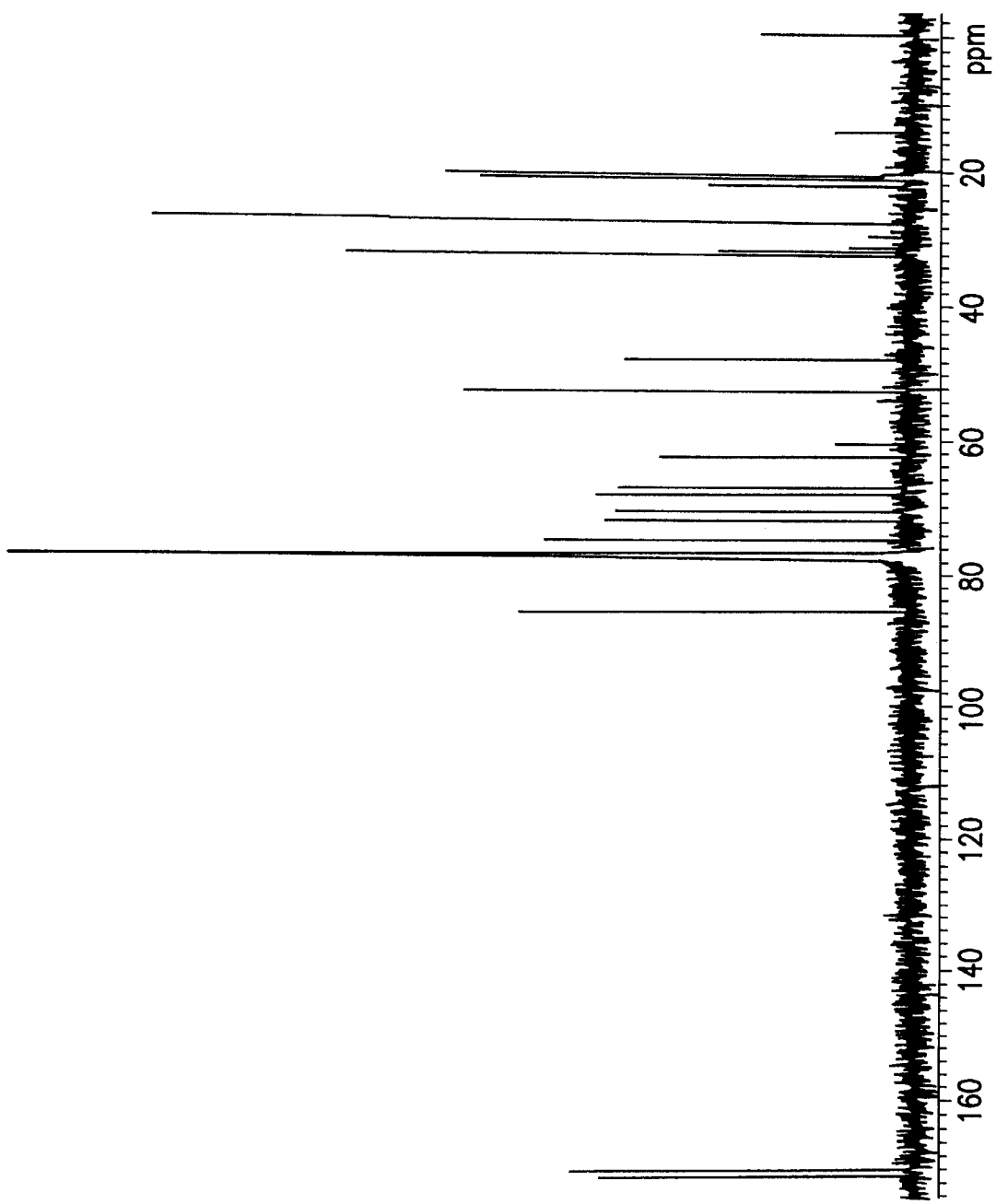
FIG. 11 is $^{13}$C-NMR spectra of Compound (12) recorded in $CDCl_3$ at 500 MHz.
Figure 12:
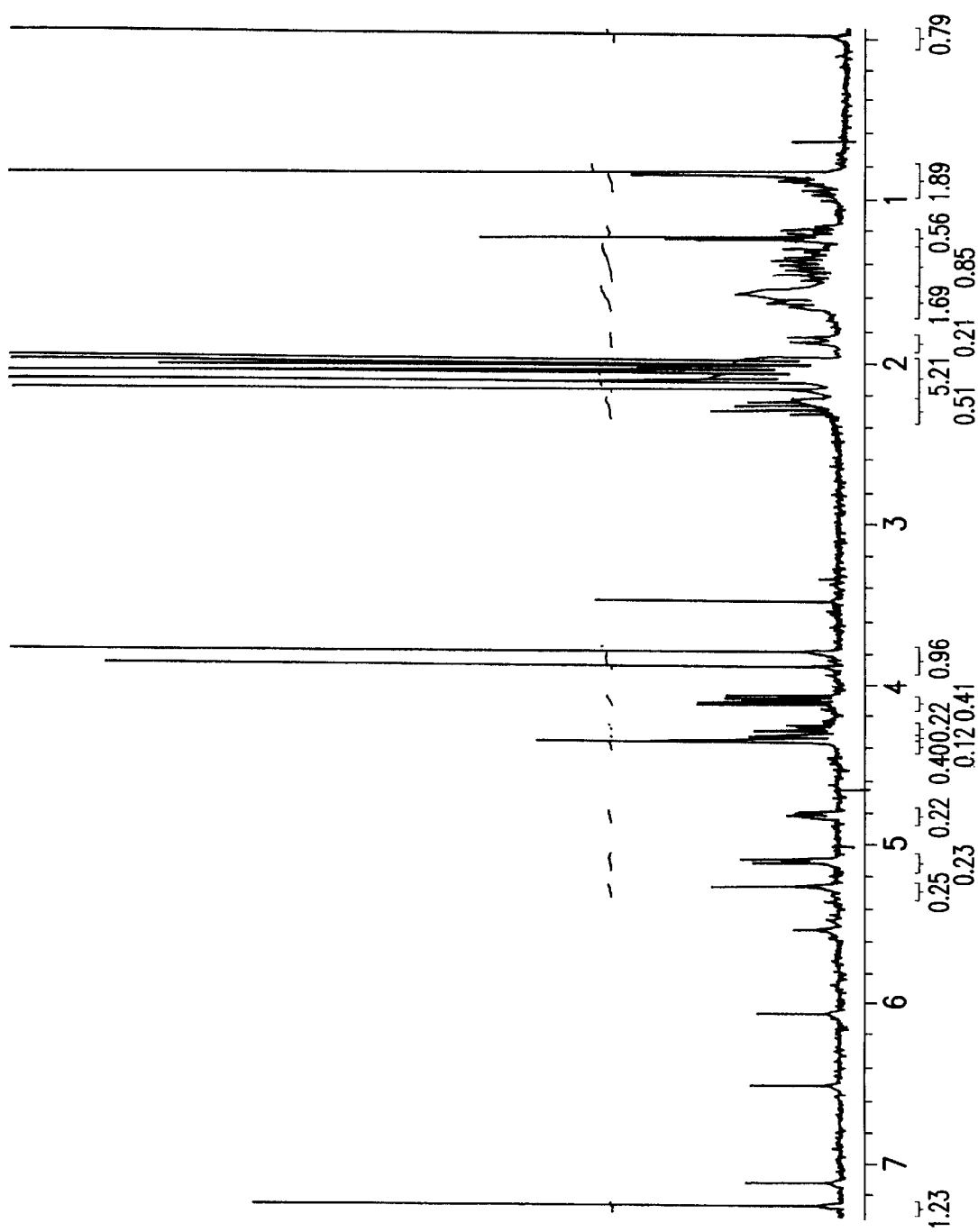
FIG. 12 is $^1$H-NMR spectra of Compound (15) recorded in $CDCl_3$ at 500 MHz.

As mentioned above, in the method of the present invention, a halogenated ulosonic acid is reacted with an aldehyde or ketone compound in the presence of a lanthanide metal halide.

As the lanthanide metal halide, halides (iodides, bromides and chlorides) of lanthanide metals may be employed. As the lanthanide metal, samarium, ytterbium and europium are preferred, and samarium is most preferred.

The reactants which react with the lanthanide metal halides are ulosonic acids such as neuraminic acids and sialic acids. Further, other carbohydrates bearing a quaternary carbon at the anomeric position (ketoses) may also be employed as the reactant to be reacted with the lanthanide metal halide. That is, the process of the present invention is directed to the process for synthesizing C-glycosides of ulosonic acids including neuraminic acids and sialic acids. The process may also be applied to the synthesis of C-glycosides carbohydrates containing a quaternary carbon, such as C-glycosides of N-acetylneuraminic acid (NANA), 3-deoxy-D-manno-octulosonic acid (KDO) and C-glycosides of 3-deoxy-D-glycero-D-galactonulosonic acid (KDN).

The halogenation may comprise replacing a hydroxyl group in the ulosonic acids such as neuraminic acid and sialic acid, or carbohydrates with a halogen atom.

Preferably, the halogen atom may be attached to the 2-position of the ulosonic acids such as neuraminic acid and sialic acid, or carbohydrates. The halogen used for the halogenation may be fluorine, chlorine, bromine and iodine, and chlorine is most preferred.

When the lanthanide metal halide is reacted with neuraminic acid or sialic acid derivatives, the reactant may be represented by the following formula [I]:

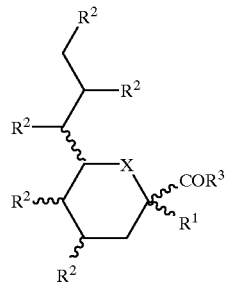

[I]

In formula [I], $R^1$ is a halogen atom.

In formula [I], each $R^2$ may be the same or different, and may be any group or atom which does not hinder the reaction, such as acyloxy groups such as those containing straight or branched alkyl groups, especially $C_1$–$C_6$ alkyl groups, benzyloxy groups, allyloxy groups, isopropylidene dioxy groups, cyclohexylidene dioxy groups, silyloxy groups or N-amide groups. Each of these groups may contain one or more, usually 1 to 5 substituents such as methyl, methoxy, benzyloxy, trichloroethoxy and trialkylsilyloxy groups. The most preferred $R^2$ is acyloxy or alkyloxy.

In formula [I], $R^3$ is not restricted at all and may be any group or atom which does not hinder the reaction. For example, $R^3$ may be straight or branched alkyloxy groups especially $C_1$–$C_6$ alkyloxy groups, cyclic alkyloxy groups, arylmethyloxy groups, arylamine groups, alkylamine groups or another carbohydrate moiety. $R^3$ may be substituted with the substituents, usually with 1 to 5 substituents, mentioned above for $R^2$.

In formula [I], X may be oxygen, alkylamine or arylamine, and methylene or substituted methylene.

Equivalents of the skeleton of the structure represented by the formula [I] may include those represented by the following formulae. The meanings of the substituents in the following formulae are as described above.

Formulae

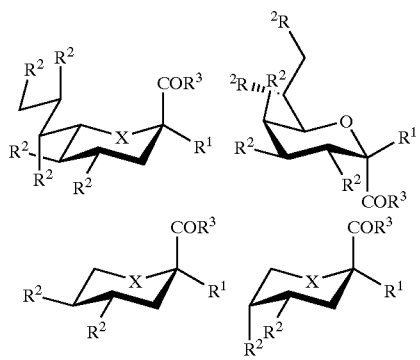

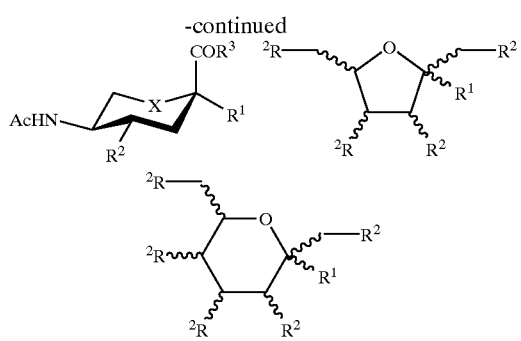

The counterpart reactant which is reacted with the above-mentioned ulosonic acids, carbohydrates containing a quaternary carbon, neuraminic acids or sialic acids, is not restricted at all and any organic compounds having an aldehyde group or ketone group may be employed. When the C-glycosides to be produced is a disaccharide, the preferred counterpart reactant may be represented by the following formula [II]:

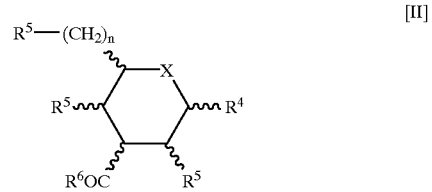

[II]

In formula [II], $R^4$ may be any group which does not hinder the reaction. The explanation about $R^3$ in formula [I] may also be applied to $R^4$.

In formula [II], $R^5$ may be the same or different, and may be any group which does not hinder the reaction. The explanation about $R^2$ in formula [I] may also be applied to $R^5$. However, benzyloxy group is also preferred in addition to acyloxy.

In formula [II], $R^6$ may be hydrogen, alkyl group or aryl group.

In formula [III], X may be oxygen, alkylamine or arylamine, and methylene or substituted methylene.

In formula [II], n=0 or 1.

Equivalents of the skeleton of the structure represented by the formula [II] may include those represented by the following formulae. The meanings of the substituents in the following formulae are as described above.

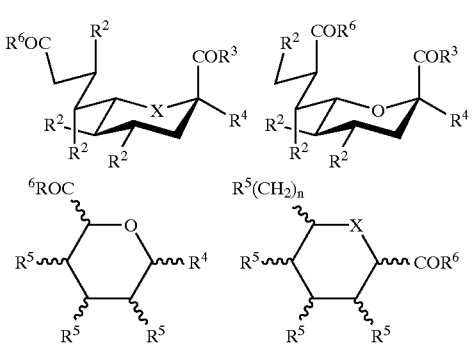

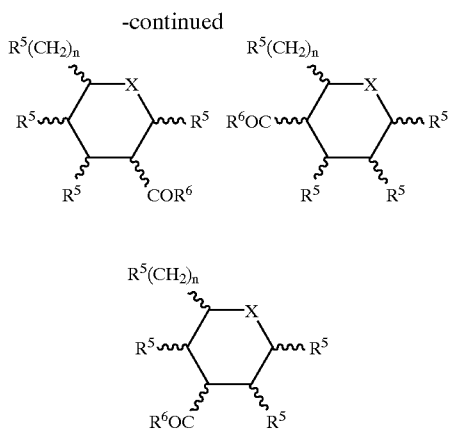

Unless otherwise specified, among any of the above-mentioned groups or substituent groups, in those which is alkyl or which may contain alkyl moiety, the number of carbon atoms may preferably be 1–6. Among any of the above-mentioned groups or substituent groups, in those which is aryl or which may contain aryl moiety, the aryl group may preferably be phenyl, naphthyl, biphenyl, anthryl or phenanthryl. The alkyl group or alkyl moiety and the aryl group or aryl moiety may contain one or more, usually 1 to 5 substituent(s) described for $R^2$.

The halogenated ulosonic acids or carbohydrates as well as the processes for producing them are known in the art, and are described in, for example, Nagy, O. J.; Bednarski, D. M.; *Tetrahedron Lett.*, 1991, 32, 3953–3956, or Morra, A; Sinaÿ, P.; Carbohydr. Res., 1989, 187, 35–42. Briefly, ulosonic acids or carbohydrates may be halogenated by treatment with acetyl chloride, acetic acid and methanol at room temperature for 24 hours.

The halogenated ulosonic acid or carbohydrate is reacted with the above-described aldehyde or ketone compound in the presence of the above-described lanthanide metal halide. As the solvent used in the reaction, not only THF, but also other aprotic solvents, such as ethers, halogenated hydrocarbons and tertiary amides such as hexamethylphosphorous triamide (HMDA) and 1,3-dimethyl-3,4,5,6-tetrahydro-2 (1H) pyrimidinone (DMPU), may be employed.

The reaction may be carried out at a temperature between −40 to 25° C., preferably 20° C. The concentration of the reactant 1 (in scheme 1 below) or reactant 8 (in scheme 2 below) or any equivalent thereof mentioned above may be from neat to 0.01 M, preferably neat. The concentration of the solution of $SmI_2$ or equivalent thereof may be 0.1 M to 0.001 M, preferably 0.1 M. The concentration of the reactant 2, 4 or 6 (in scheme 1) or reactant 9 or 11 (in scheme 2) or any equivalent thereof mentioned above may be from neat to 0.01 M, preferably neat. The mixing ratio of reactant 1 or 8 (or equivalent thereof): reactant 2, 4, 6, 9 or 11 (or equivalent thereof): lanthanide metal halide may preferably be 1:(0.2–10):(0.5–20), more preferably 1:(0.5–5):(1–10), still more preferably 1:(1–2):(2–4) in terms of molar equivalence. The reaction time may be 1 min. to 1 hr, preferably 30 min.

The C-glycosides of the ulosonic acids or carbohydrates prepared by the method of the present invention may be used as pharmaceuticals and cosmetics, such as antibacterial agents, antiviral agents, antitumor agents by attaching the C-glycosides to a known antibacterial agents, antiviral agents or antitumor agents, since the C-glycosides are non-hydrolyzable in cells. The C-glycosides of the ulosonic acids or carbohydrates prepared by the method of the present invention may also be used as vaccines with increased stability.

The invention will now be described by way of examples thereof. It should be noted that the examples are presented for the illustration purpose only and should not be interpreted in any restrictive way.

EXAMPLES

In this example, we describe a new finding, that the ulosonic acid containing C-glycosylation method developed in our laboratory can be performed with the 2-chloro-derivatives of NANA, KDN and KDO.

KDN and KDO were prepared according to previously described methods.[10] Glycosyl chloride derivatives of KDN and KDO were synthesized using a similar procedure to that used for preparing NANA-glycosyl chloride. NANA-glycosyl chloride (1) and ketone (2) (1.2 equiv.) were reacted in an inert atmosphere with 4 equiv. of freshly prepared 0.1 M $SmI_2$ solution in THF at room temperature. We found that 2.5 equiv. of $SmI_2$ is the minimum amount for this reaction while 4 or more equiv. gave the best yields. This reaction results in a nearly instantaneous conversion to the desired C-glycoside of NANA (3) in 95% yield (Scheme1).

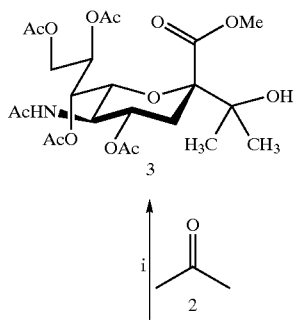

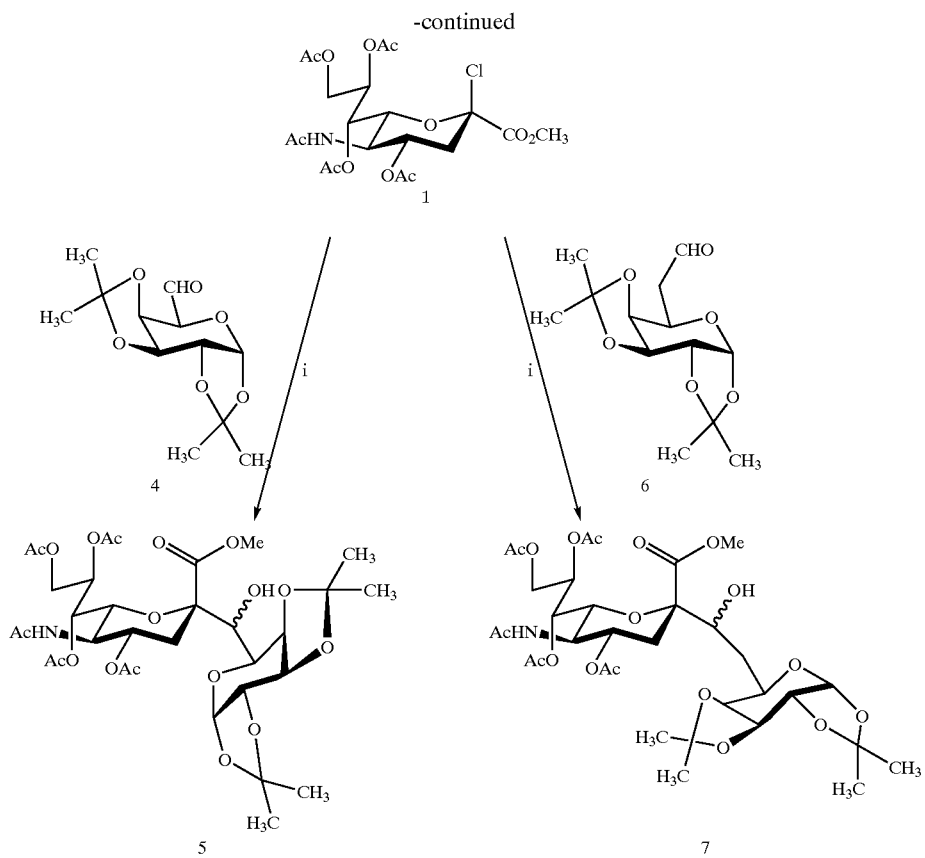

Scheme 1 i. 4 Equiv of SmI$_2$(0.1 M in THF)

Next, a very efficient synthesis of C-disaccharides (5) and (7) was performed using the above stratagem. Coupling of the glycosyl chloride (1) and sugar aldehydes (4) or (6) again instantaneously generated the desired α-C-disaccharides (5) and (7) in an 88% and >95% yield respectively, based on NANA. Empirical rules[11] and $^1$H-$^{13}$C decoupling experiments[8b] were used to deduce the α-configuration of these products. The H-4 signals in both (5) (4.57–4.62 ppm) and (7) (4.74–4.84 ppm) are observed at <5.00 ppm (in the β-anomer H-4 should be observed at >5.00 ppm). Little or no stereocontrol was observed at the newly formed stereo-center on the hydroxymethylene bridge. C-disaccharide (5) was formed in a 3:1 diastereomeric mixture while C-disaccharide (7) was obtained as a 1:1 diastereometric mixture (Scheme 1).

The reaction leading to NANA α-C-glycosides were next examined using KDN and KDO glycosyl chlorides. As we expected, KDN α-C-glycosides and KDO β-C-glycosides were afforded in excellent yield respectively (Scheme 2). The α-selectivity at the anomeric configuration and the S-configuration[8a] of alcohol in C-disaccharide (10) are confirmed by empirical rules, molecular modeling and IRMA calculation based on NMR data (2D ROESY and $^{13}$C NMR).[9]

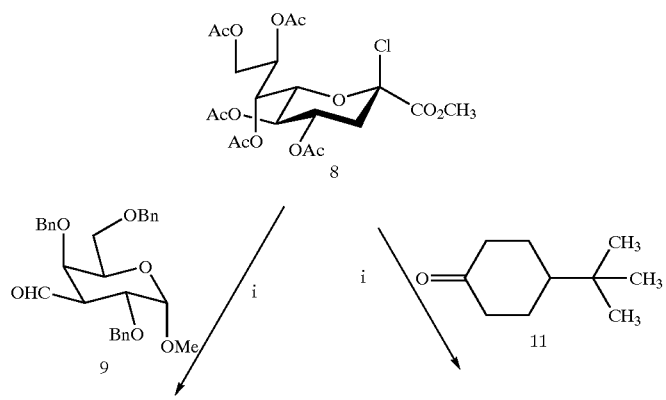

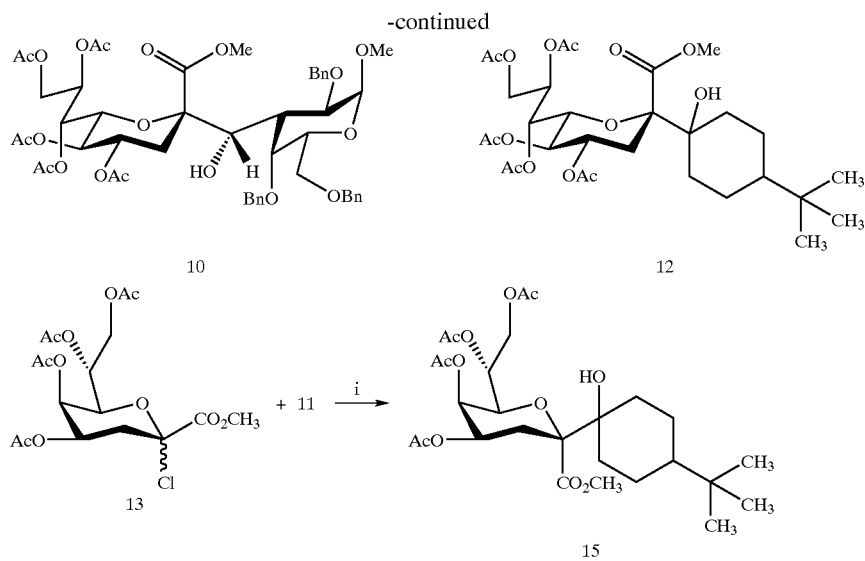

Scheme 2 i. 4 Equiv of SmI$_2$(0.1 M in THF)

KDO-C-glycosides have been previously synthesized through the alkylation of the ester enolate giving β-stereoselectivity.[12] The C-glycosylation of (13) is stereospecific forming a single C-glycoside (15). $^1$H-$^{13}$C decoupling experiments[13] were done to assign the anomeric configuration of KDO-C-glycoside. Some empirical $^1$H-NMR rules have been used for deducing the anomeric configurations of KDO derivatives. However, these rules often lead to ambiguous assignment. This is due to the fact that the substituents can greatly influence the chemical shifts of the neighboring protons.[14] A definitive determination of the anomeric configurations of KDO derivatives can be achieved by comparison of the proton-coupled $^{13}$C-NMR signals of the C-1 in α- and β-anomers.[15] In the typical $^5C_2$ chair conformation of KDO derivatives, the dihedral angels of (C-1)–(C-2)–(C-3)–(H-3ax) in α- and β-anomers are nearly 60° and 180°, respectively. Therefore α-anomeric configuration would give a small value for the coupling constant between C-1 and H-3ax ($J_{C-1, H-3ax}$<1 Hz) and the β-anomer would give a relatively large coupling constant ($J_{C-1, H-3ax}$=5–6 Hz) according to Karplus relationship.[16] The $J_{3ax,4}$=12.5 Hz and $J_{3eq,4}$=4.9 Hz confirmed that KDO-C-glycoside is in the $^5C_2$ conformation and also the $^3J$ coupling constant of $J_{C-1, H-3ax}$=6.0 Hz confirmed that KDO-C-glycoside is in the β configuration.

Suplementary Material

2. Experimental

General methods. Melting points were uncorrected. Optical rotations were measured with a Perkin Elmer 141 polarimeter at ambient temperature. $^1$H NMR (500 MHz) spectra were acquired using a Varian Unity-500 spectrometer equipped with a VXR 5000 computer system. Mass spectra were obtained using a VG ZAB-HF instrument in fast-atom bombardment (FAB) ionization mode. All reactions were monitored by thin-layer chromatography on aluminum sheets, Silica Gel 60 F$_{254}$ (E. Merck); detection under short wavelength UV light (254 nm) or by dipping the plates into staining solution (1.0 g cerium ammonium sulfate and 24.0 g ammonium molybdate in 31 mL sulfuric acid and 470 mL water) then heating. Flash chromatography was performed using 230–400 mesh silica gel 60. All solvents and reagents were obtained from Aldrich Chemical Co. (Milwaukee, Wis., USA).

General procedure for C-glycosidation. Glycosyl chlorides (Neu5Ac, KDN, KDO) (150 mg) and 1.2–2.0 equiv. of electrophile (ketone or sugar aldehyde) were dried together under high vacuum for 4 h, then dissolved in degassed anhydrous THF (0.5–1 mL). SmI$_2$ (4 equiv., freshly prepared from Sm and ICH$_2$CH$_2$I, 0.1 M in THF) was added in one portion at room temperature with vigorous stirring. After 10 min, the reaction mixture was directly filtered, and the filtrate was concentrated under reduced pressure, then purified on silica gel column with EtOAc as eluent.

Methyl 5-acetamido-4, 7,8,9-tetra-O-acety-2, 6-anhydro-3, 5-dideoxy-2-(C-1-hydroxy-Acet-1-yl)-D-erythro-L-monno-nononate (3). The C-disaccharide was obtained (95% yield) from the reaction of 1 with ketone 2 using the general procedure described above. The product was obtained by flash column chromatography using 2:1 petroleum ether EtOAc as eluent: $[α]_D^{20}$–14° (c 0.3, CHCl$_3$); $^1$H NMR (CDCl$_3$): 1.20, 1.30 (2s, 2×3H, C (CH$_3$)$_2$), 1.95 (t, 1H $J_{3a, 3eq}$=12.5 Hz, $J_{3a,4}$=12.5 Hz, H-3$_{ax}$), 1.98, 2.02, 2.03, 2.11, 2.18 (5s, 5×3H, 5Ac) 2.55 (dd, 1H, $J_{3eq, 4}$=2.1 Hz, H-3$_{eq}$), 3.80 (s,3H, COOCH$_3$), 4.00–4.20 (m, 3H, H-5, H-6, H-9a), 4.38 (dd, 1H,$J_{8,9b}$=1.2 Hz, $J_{9a,9b}$=11.6 Hz, H-9b), 4.80 (ddd, 1H, $J_{3ax,4}$=$J_{4,5}$=12.5, $J_{4,NH}$=8.9 Hz, H-4), 5.30 (d, 1H, NH), 5.40–5.45 (m, 1H, H-7), 5.52–5.60 (m, 1H, H-8). HRFABMS calcd for C$_{23}$H$_{35}$NO$_{13}$(M+Na)$^+$: 556.2019. Found: m/z 556.2006 (M+Na)$^+$.

10-Acetamido-9, 12,13,14-tetra-O-acetyl-7, 11-anhydro-8, 10-dideoxy-7-(C-Methoxycarbonyl)-1,2:3,4-di-O-isopropylidene-D-arabino-L-gulo-(L-ido)-D-galacto-tetradeca-1, 5-pyranose (5). The C-disaccharide was obtained (88% yield) from the reaction of 1 with sugar aldehyde 4 using the general procedure described above. A small amount of pure major isomer was obtained by flash column chromatography using 1:3 petroleum ether-EtOAc as a eluent: $[α]_D^{20}$–3.7° (c 0.4, CHCl$_3$); $^1$H NMR (CDCl$_3$): (major isomer)1.32, 1.38, 1.50, 1.53, 1.86, 2.03, 2.05, 2.13, 2.17 (9s, 9×3H), 2.63 (dd, 1H), 3.14 (d, 1H), 3.60 (d, 1H), 3.79 (s, 3H), 3.90–3.96 (m, 2H), 4.03 (t, 1H), 4.10 (dd, 1H), 4.13 (dd, 1H), 4.28 (br s, 2H), 4.30 (dd, 1H), 4.48 (d, 1H), 4.58 (dd, 1H), 4.76 (ddd, 1H), 5.12 (d, 1H), 5.29 (d, 1H), 5.47 (br d, 1H), 5.52 (d, 1H). HRFABMS calcd for C$_{32}$H$_{48}$NO$_{18}$ (M+H): 734.2871. Found: m/z 734.2881 (M+H).

11-Acetamido-10, 13,14,15-tetra-O-acetyl-8, 12-anhydro-9, 11-dideoxy-7-(C-Methoxycarbonyl)-1,2:3,4-di-O-isopropylidene-D-arabino-L-gulo-(L-ido)-D-galacto-tetradec-1, 5-pyranose (7). The C-disaccharide was obtained (>95% yield) from the reaction of 1 with sugar aldehyde 6 using the general procedure described above. The product was obtained by flash column chromatography using 2:1 petroleum ether EtOAc as eluent: $[\alpha]_D^{20}$ –3.7° (c 0.4, CHCl$_3$); $^1$H NMR (CDCl$_3$): (R,S mixture), 1.31, 1.38, 1.40, 1.47, 1.50, 1.54, 1.56 (8s, 1H), 1.75 (t, 1H, H-3$_{eq}$), 1.88 (t, 1H, H-3$_{eq}$), 2.01, 2.02, 2.03, 2.04, 2.05 (5s, 5×3H, 5Ac), 2.13, 2.14, 2.15, 2.16, 2.18 (5s, 5×3H, 5Ac), 2.38 (dd, 1H, H-3$_{ax}$), 2.47 (dd, 1H, H-3$_{3ax}$), 3.77 (s, 3H, COOCH$_3$), 3.79 (s, 3H, COOCH$_3$), 3.87–4.40 (m, 22H, H-2', H-3', H-4', H-5', H-6', H-6, H-9a, H-9b, H-5, H-7"), 4.62 (dd, 2H, H-1'), 4.74–4.84 (m, 2H, H-4), 5.07 (dd, 2 NHAc), 5.30–5.36 (m, 2H, H-7), 5.42–5.85 (m, 2H, H-8). HRFABMS calcd for C$_{33}$H$_{498}$NO$_{18}$ (M+Na)$^+$: 770.2853. Found: m/z 770.2847 (M+Na)$^+$.

Methyl-4, 5,7,8,9-penta-O-acetyl-2, 6-anhydro-3-deoxy-2-C {(S)-hydroxy-[methyl 2,4,6-tri-O-benzyl-3-deoxy-α-D-galactopyranosidyl)]-methyl}-D-erythro-L-monno-nononate (10). The C-disaccharide was obtained (>90% yield) from the reaction of 8 with sugar aldehyde 9 using the general procedure described above. The product was obtained by flash column chromatography using 2:1 petroleum ether-EtOAc as eluent: $[\alpha]_D^{20}$ –48° (c 0.1, CHCl$_3$); $^1$H NMR (CDCl$_3$): δ=1.977, 2.008, 2.011, 2.030, 2.158 (5s, 15H, 5 COCH$_3$), 2.05 (dd, 1H, J$_{3ax, 3eq}$=13.1 Hz, J$_{3'ax, 4'}$=11.0 Hz, H-3ax), 2.57 (dd, 1H, J$_{3'eq, 4'}$=4.8 Hz, H-3'eq), 2.74 (bd, 1H, J$_{2,3}$=6.4 Hz, J$_{3,4}$ and J$_{3,3''}$<0.5 Hz, H-3) 3.45 (s, 3H, OCH$_3$), 3.56–3.60 (m, 2H, 2H-6), 3.76 (s, 3H, COOCH$_3$), 3.88 (bs, 1H, H-3"), 3.97 (dd, 1H, J$_{1,2}$=3.2 Hz, J$_{2,3}$=6.0 Hz, H-2), 4.00 (dd, 1H, J$_{5',6'}$=10.3 Hz, J$_{6',7'}$=1.8 Hz, H-6'), 4.05 (dd, 1H, J$_{9'a, 9'b}$=12.5 Hz, J$_{8',9'a}$=5.4 Hz, H-9'a), 4.27 (dd, 1H, J$_{8', 9'b}$=2.3 Hz, H-9'b), 4.37–4.40 (m, 2H, H-5 and OH at C3"), 4.41, 4.61 (2d, 2H, J=12.6 Hz, PhCH$_2$—), 4.45, 4.64 (2d, 2H, J=12.0 Hz, PhCH$_2$—), 4.47 (bs, 1H, J$_{4,5}$<0.5 Hz, H-4) 4.51, 4.58 (2d, 2H, J=12.4 Hz, PhCH$_2$—), 4.73 (d, 1H, H-1), 4.82 (t, 1H, J$_{4',5}$=J$_{5',6'}$=10.3 Hz, H-5'), 4.95 (ddd, 1H, H-4'), 5.31 (dd, 1H, J$_{7,8}$=8.6 Hz, H-7'), 5.42 (dd, 1H, H-8'), 7.20–7.40 (m, 15H, 3 Ph.). HRFABMS calcd for C$_{49}$H$_{60}$NO$_{19}$ (M+Na)$^+$: 975.3627. Found: m/z 975.3635 (M+Na)$^+$ Methyl-4, 5,7,8,9-penta-O-acetyl-2, 6-anhydro-3-deoxy-2-C-(1-hydroxy-tert-butyl cyclohex-1-yl)-D-erythro-L-monno-nononate (12). The C-disaccharide was obtained (95% yield) from the reaction of 8 with ketone 11 using the general procedure described above. The product was obtained by flash column chromatography using 2:1 petroleum ether-EtOAc as eluent: $[\alpha]_D^{20}$ –38° (c 0.1, CHCl$_3$); $^1$H NMR (CDCl$_3$): 0.92 (s, 9H, C(CH$_3$)$_3$), 0.95–1.86 (m, 10H, cyclohexyl H and OH), 1.97 (t,1H, J$_{3ax, 3eq}$=J$_{3ax, 4}$=13.4 Hz, H-3ax), 2.00 (s, 6H, 2, CH$_3$CO), 2.05, 2.09, 2.19 (3s, 3×3H, 3 CH$_3$CO) 2.55 (dd, 1H, J$_{3eq, 4}$=1.8 Hz, H-3eq), 3.81 (s, 3H, COOCH$_3$), 4.09 (dd, 1H, J$_{5,6}$=9.6 Hz, J$_{6,7}$<1 Hz, H-6), 4.13 (dd, 1H, J$_{9A,9B}$=12.1 Hz, J$_{8,9A}$=5.1 Hz, H-9A), 4.27 (d, 1H, J$_{8,9B}$<1 Hz, H-9B) 4.79 (t, 1H, J$_{4,5}$=J$_{5,6}$=9.6 Hz, H-5), 4.84 (ddd, 1H, H-4) 5.33 (d, 1H, J$_{7,8}$=8.9 Hz, H-7), 5.41–5.47 (m, 1H, H-8). HRFABMS calcd for C$_{30}$H$_{46}$NO$_{14}$ (M+Na)$^+$: 653.2785. Found: n/z 653.2809 (M+Na)$^+$.

Methyl-4, 5,7,8-tetra-O-acetyl-3-deoxy-2-C-(1-hydroxy-tert-butyl cyclohex-1-yl)-β-D-monno-2-octulopyronaside) onate. (15). The C-disaccharide was obtained (85% yield) from the reaction of 13 with ketone 11 using the general procedure described above. The product was obtained by flash column chromatography using 2:1 petroleum ether-EtOAc as a eluent: $^1$H NMR (CDCl$_3$): 0.89 (s, 9H, C(CH$_3$)$_3$), 0.97–1.90 (m, 10H, cyclohexyl and OH), 1.98, 2.01, 2.07, 2.12 (4s, 12H, 4 COCH$_3$), 2.26 (dd, 1H, J$_{3eq, 4}$=4.94 Hz, H-3eq), 2.31 (t, 1H, J$_{3ax, 4}$=12.5 Hz, H-3$_{ax}$), 3.81 (s, 3H, COOCH$_3$), 4.09 (dd, 1H, J$_{6,7}$=5.12 Hz, H-6), 4.27 (dd, 1H, J$_{8a,8b}$=13.1 Hz, J$_{8,7}$=7.33 Hz, H-8a), 4.36 (d, 1H, J$_{7,8b}$=3.48 Hz, H-8b), 4.78–4.84 (m, 1H, H-4), 5.09–5.14 (m, 1H, H-7), 5.27 (bs, 1H, H-5). $^{13}$C NMR: 171.3, 171.06, 171.61, 170.3, 170.09 (C-1 and 4 Ac), 86.5 (C-2), 71.2 (C-6), 70.6 (C-5), 68.72 (C4), 66.7 (C-8), 52.7 (OCH$_3$). HRFABMS calcd for C$_{27}$H$_{42}$O$_{12}$ (M+Na)$^+$ 558.6220. found: m/z 558.6217 (M+Na)$^+$.

This study demonstrates a new simple procedure for the C-glycosylation of ulosonic acids through their chloro-derivatives under Barbier conditions.

REFERENCES AND NOTES (1) Varki, A., Glycobiology, 1992, 2, 25.
(2) Wei, A.; Haudrechy, A.; Audin, C.; Jun, C-H.; Haudrechy-Bretel, N.; Kishi, Y., *J. Org. Chem.*, 1995, 60, 2160 and the references cited therein.
(3) a) Du, Y.; Vlahov, I. R.; Linhardt, R. J., *Tetrahedron*, 1998, 54, 9913–9959. b) Sinaÿ, P., *Pure & Appl. Chem.* 1997, 69, 459–463. c) Beau, J.-M.; Gallagher, T., *Topics Curr. Chem.* 1997, 187, 1–54. d) Nicotra, F., Topics Curr. Chem. 1997, 187, 55–83. e) Postema, M. H. D. , *C-Glycoside Synthesis;* CRC press: Boca Raton, 1995. f) Levy, D. E.; Tang, C., *The Chemistry of C-glycosides;* Pergamon: Oxford, 1995.
(4) Pouilly, P.; de Chenede, A.; Mallat, J. M.; Sinaÿ, P., *Bull. Soc. Chim. Fr.* 1993, 130, 256.
(5) Hung, C-S.; Wong, C-H. *Tetrahedron Lett,* 1996, 37, 4903–4906.
(6) Nagy, O. J.; Bednarski, D. M.; *Tetrahedron Lett.,* 1991, 32, 3953–3956; Morra, A.; Sinaÿ, P.; Carbohydr. Res., 1989, 187, 35–42.
(7) Mazeas, D.; Skrydstrup, T.; Beau, J.-M., *Angew. Chem. Int. Ed. Engl.* 1995, 34, 909–912.
(8) a) Vlahov, I. R.; Vlahova, P. I.; Linhardt, R. J., *J. Am.Chem. Soc.* 1997, 119, 1480. b) Du, Y.; Linhardt, R. J., *Carbohydr. Res.,* 1998, 308, 161–164.
(9) Du. Y.; Polat. T.; Linhardt, R. J., Tetrahedron Lett., 1998, 39, 5007–5010.
(10) Shirai, R.; Ogura, H.; *Tetrahedron Lett.,* 1989, 30, 2263–2264.
(11) Kanie, O.; Kiso, M.; Hasegawa, A., *J. Carbohydr. Chem.* 1988, 7, 501–506.
(12) Norbeck, D. W.; Kramer, J. B.; Lartey P. A., *J. Org. Chem.,* 1987, 52, 2174–2179.
(13) General procedure: Glycosyl chloride (50 mg) and 1.2–2.0 equiv. of electrophile (ketone or sugar aldehyde) were dried together under high vacuum for 4 h SmI$_2$ (4 equiv. freshly prepared from Sm and ICH$_2$CH$_2$I, 0.1 M in THF) was added in one portion at room temperature. The reaction mixture was concentrated under reduced pressure after 5 min, then purified on silica gel column with EtOAc as eluent. All new compounds were confirmed by NMR and HR FABMS. Selected HRFABMS and $^1$H-NMR data [values of δ$_H$ at 500 MHz measured in CDCl$_3$: 3 1.20, 1.30 (2s, 2×3 H, C (CH$_3$)$_2$), 1.95 (t, 1H J$_{3a, 3eq}$=12.5 Hz, J$_{3a, 4}$=12.5 Hz, H-3$_{ax}$), 1.98, 2.02, 2.03, 2.11, 2.18 (5s, 5×3H, 5Ac) 2.55 (dd, 1H, J$_{3eq, 4}$=2.1 Hz, H-3$_{eq}$), 3.80 (s, 3H, COOCH$_3$), 4.00–4.20 (m, 3H, H-5, H-6, H-9a), 4.38 (dd,1H,J$_{8,9b}$=1.2 Hz, J$_{9a, 9b}$=11.6 Hz, H-9b), 4.80 (ddd, 1H, J$_{3ax,4}$=J$_{4,5}$=12.5, J$_{4,NH}$=8.9 Hz, H-4), 5.30 (d, 1H, NH), 5.40–5.45 (m, 1H, H-7), 5.52–5.60 (m, 1H, H-8). HRFABMS calcd for C$_{23}$H$_{35}$NO$_{13}$ (M+Na)$^+$: 556.2019. Found: m/z 556.2006 (M+Na)$^+$. 7 (R,S mixture), 1.31, 1.38, 1.40, 1.47, 1.50, 1.54, 1.56 (8s, 12H), 1.75 (t, 1H, H-3$_{eq}$), 1.88 (t, 1H, H-3$_{eq}$), 2.01, 2.02, 2.03, 2.04, 2.05 (5s, 5×3H, 5Ac), 2.13, 2.14, 2.15, 2.16, 2.18 (5s, 5×3H, 5Ac), 2.38 (dd, 1H, H-3$_{ax}$), 2.47 (dd, 1H, H-3$_{ax}$), 3.77 (s, 3H, COOCH$_3$), 3.79 (s, 3H, COOCH$_3$), 3.87–4.40 (m, 22H, H-2', H-3', H-4', H-5', H-6', H-6, H-9a, H-9b, H-5, H-7"), 4.62 (dd, 2H, H-1'), 4.74–4.84 (m, 2H, H-4), 5.07 (dd, 2 NHAc), 5.30–5.36 (m, 2H, H-7), 5.42–5.85 (m, 2H, H-8) HRFABMS calcd for C$_{33}$H$_{498}$NO$_{18}$ (M+Na)$^+$: 770.2853. Found: m/z 770.2847 (M+Na)$^+$. 15 0.89 (s, 9H, C(CH$_3$)$_3$), 0.97–1.90 (m, 10H, cyclohexyl and OH), 1.98, 2.01, 2.07, 2.12 (4s, 12H, 4 COCH$_3$), 2.26 (dd, 1H, J$_{3eq, 4}$=4.94 Hz, H-3$_{eq}$), 2.31 (t, 1 H, J$_{3ax, 4}$=12.5 Hz, H-3$_{ax}$), 3.81 (s, 3H, COOCH$_3$), 4.09 (dd, 1H, J$_{6,7}$=5.12 Hz, H-6), 4.27 (dd, 1H, J$_{8a,8b}$=13.1 Hz, J$_{8,7}$=7.33 Hz, H-8a), 4.36 (d, 1H, J$_{7,8b}$=3.48 Hz, H-8b), 4.78–4.84 (m, 1H, H-4), 5.09–5.14 (m, 1H, H-7), 5.27 (bs, 1H, H-5). HRFABMS calcd for C$_{27}$H$_{42}$O$_{12}$ (M+Na)$^+$558.6220. found: m/z 558.6217 (M+Na)$^+$. $^{13}$C NMR: 171.3, 171.06, 171.61, 170.3, 170.09 (C-1 and 4 Ac), 86.5 (C-2), 71.2 (C-6), 70.6 (C-5), 68.72 (C-4), 66.7 (C-8), 52.7 (OCH$_3$).

(14) Li, Y-T.; Wang, L-X.; Pavlova, V. N.; Li, S-C.; Lee, Y. C., *J. Biol. Chem.*, 1997, 272, 26419–26424.

(15) Unger, F. M.; Stix, D.; Schulz, G., *Carbohydr. Res.*, 1980, 80, 191–195.

(16) Schwarcz, J. A.; Perlin, A. S., *Can. J. Chem.* 1972, 50, 3667–36670.

What is claimed is:

1. A method for synthesizing C-glycosides of ulosonic acids comprising the step of reacting a halogenated ulosonic acid with an aldehyde or ketone compound in the presence of a lanthanide metal halide.

2. A method for synthesizing C-glycosides of carbohydrates containing a quaternary carbon comprising the step of reacting a halogenated carbohydrate containing a tertiary carbon with an aldehyde or ketone compound in the presence of a lanthanide metal halide.

3. A method for synthesizing C-glycosides of neuraminic acids or sialic acids comprising the step of reacting a protected halogenated neuraminic acid or sialic acid with an aldehyde or ketone compound in the presence of a lanthanide metal halide.

4. A method for synthesizing C-glycosides of 3-deoxy-D-manno-octulosonic acid (KDO) comprising the step of reacting a protected halogenated 3-deoxy-D-manno-octulosonic acid with an aldehyde or ketone compound in the presence of a lanthanide metal halide.

5. A method for synthesizing C-glycosides of 3-deoxy-D-glycero-D-galactonulosonic acid (KDN) comprising the step of racting a protected halogenated 3-deoxy-D-glycero-D-galactonulosonic acid with an aldehyde or ketone compound in the presence of a lanthanide metal halide.

6. A method for synthesizing C-glycosides of N-acetyl neuraminic acid (NANA) comprising the step of reacting a protected halogenated N-acetyl neuraminic acid with an aldehyde or ketone compound in the presence of a lanthanide metal halide.

7. The method according to any one of claims 1 to 6, wherein said lanthanide metal halide is a halide of samarium (II).

8. The method according to claim 7, wherein said halide is SmI$_2$.

9. The method according to claim 1, wherein said halogenated ulosonic acid is a chlorinated ulosonic acid.

10. The method according to claim 1, wherein said halogenated ulosonic acid is prepared by a method comprising replacing a hydroxyl group in said ulosonic acid with a halogen atom.

11. The method according to claim 10, wherein said halogen atom is attached to the 2-position of said ulosonic acid.

12. The method according to claim 3, wherein said protected halogenated neuraminic acid or sialic acid is represented by the formula [I]:

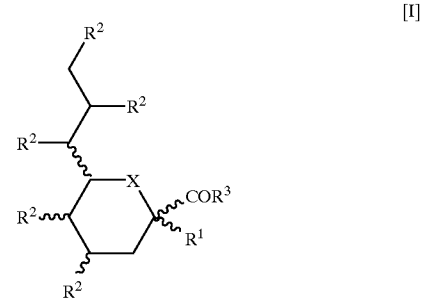

(wherein R$^1$ is a halogen; R$^2$ independently is any group or atom which does not hinder the reaction; R$^3$ is any group or atom which does not hinder the reaction; and X is oxygen, alkylamine, arylamine, methylene or substituted methylene).

13. The method according to any of claims 1 to 6, wherein said aldehyde or ketone is represented by the formula [II]:

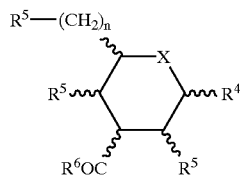

(wherein R$^4$ is any group which does not hinder the reaction; R$^5$ independently is any group which does not hinder the reaction; R$^6$ is hydrogen, alkyl group or aryl group; X is oxygen, alkylamine or arylamine, methylene or substituted methylene; n is an integer of 0 or 1).

14. The method according to claim 3, wherein said protected halogenated neuraminic acid or sialic acid are represented by the following formulae:

Formulae

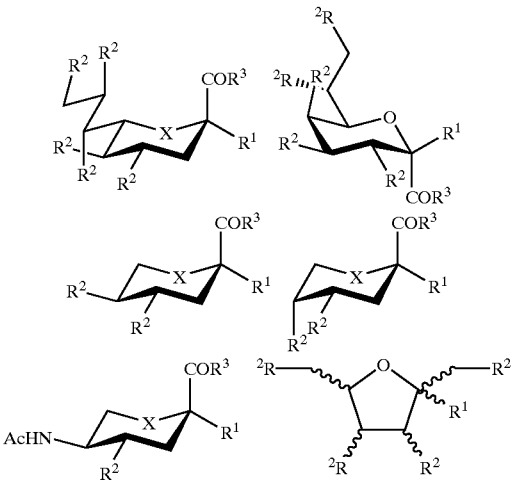

-continued

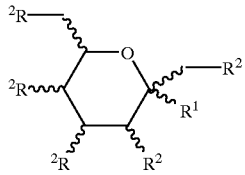

wherein $R^1$ is a halogen, $R^2$ independently is any group or atom which does not hinder the reaction; $R^3$ is any group or atom which does not hinder the reaction; and X is oxygen, alkylamine, arylamine, methylene or substituted methylene.

15. The method according to any one of claims 1 to 6, wherein said aldehyde or ketone is represented by one of the following formulae:

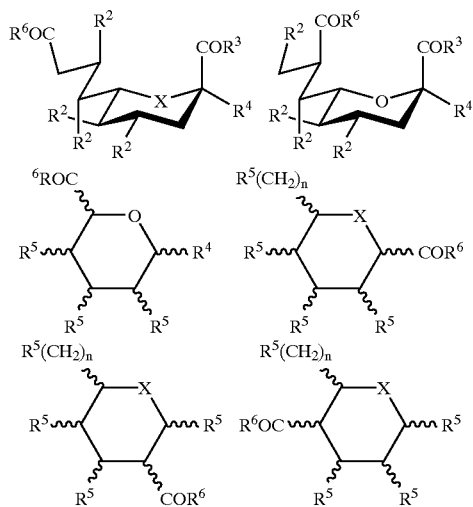

-continued

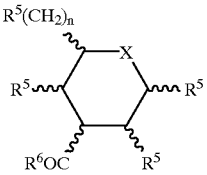

wherein $R^1$ is a halogen, $R^2$ independently is any group or atom which does not hinder the reaction; $R^3$ is any group or atom which does not hinder the reaction; and X is oxygen, alkylamine, arylamine, methylene or substituted methylene.

16. The method according to claim 2, wherein said halogenated carbohydrate is obtained by a process comprising replacing a hydroxyl group in said carbohydrate with a halogen atom.

17. The method according to claim 16, wherein said halogen atom is attached to the 2-position of said carbohydrate.

18. The method according to claim 3, wherein said halogenated neuraminic acid or sialic acid is obtained by a process comprising replacing a hydroxyl group in said neuraminic acid or sialic acid with a halogen atom.

19. The method according to claim 18, wherein said halogen atom is attached to the 2-position of said neuraminic acid or sialic acid.

20. The method according to claim 1, wherein said halogenated ulosonic acid is obtained by reacting an ulosonic with acetyl chloride, acetic acid and methanol at room temperature for 24 hours.

21. The method according to claim 2, wherein said halogenated carbohydrate is obtained by reacting a carbohydrate with acetyl chloride, acetic acid and methanol at room temperature for 24 hours.

22. The method according to claim 3, wherein said halogenated neuraminic acid or sialic acid is obtained by reacting a neuraminic acid or sialic acid with acetyl chloride, acetic acid and methanol at room temperature for 24 hours.

* * * * *